United States Patent
Jung et al.

(10) Patent No.: US 9,273,212 B2
(45) Date of Patent: Mar. 1, 2016

(54) NATURAL ANTIBACTERIAL WATERPROOF COMPOSITION FOR SOIL AND WOOD AND METHOD FOR MANUFACTURING THE SAME

(71) Applicants: Ean Ki Jung, Gyeongsanbuk-do (KR); Soe Ho Jung, Gyeongsanbuk-do (KR)

(72) Inventors: Ean Ki Jung, Gyeongsanbuk-do (KR); Soe Ho Jung, Gyeongsanbuk-do (KR)

( * ) Notice: Subject to any disclaimer, the term of this patent is extended or adjusted under 35 U.S.C. 154(b) by 0 days.

(21) Appl. No.: 14/620,794

(22) Filed: Feb. 12, 2015

(65) Prior Publication Data

US 2015/0225573 A1    Aug. 13, 2015

(30) Foreign Application Priority Data

Feb. 13, 2014    (KR) ......................... 10-2014-0016560

(51) Int. Cl.
| | | |
|---|---|---|
| *C09D 5/14* | (2006.01) | |
| *A01N 65/00* | (2009.01) | |
| *C09K 3/18* | (2006.01) | |
| *B27K 3/34* | (2006.01) | |
| *C09K 3/22* | (2006.01) | |

(52) U.S. Cl.
CPC  *C09D 5/14* (2013.01); *A01N 65/00* (2013.01); *B27K 3/34* (2013.01); *C09K 3/18* (2013.01); *C09K 3/22* (2013.01)

(58) Field of Classification Search
CPC ....... A01N 65/00; A01N 65/24; A01N 27/00; A01N 65/08; A01N 2300/00; C09D 191/005; C09D 191/06; C09D 193/00; C09D 193/02; C09D 5/14; C09K 3/18; C09K 3/22; B27K 3/34
USPC .................................................... 106/2, 15.05
See application file for complete search history.

(56) References Cited

FOREIGN PATENT DOCUMENTS

| KR | 20030077473 | 10/2003 |
|---|---|---|
| KR | 20090025623 | 3/2009 |
| KR | 101419895 | 7/2014 |

*Primary Examiner* — Anthony J Green
(74) *Attorney, Agent, or Firm* — IPLA P.A.; James E. Bame

(57) ABSTRACT

A natural antibacterial waterproof composition for soil and wood and a method for manufacturing includes beef tallow, soybean oil, turpentine, pine resin, paraffin, and a natural antibacterial insecticide, wherein the natural antibacterial insecticide is made by extracting effective components from ginkgo leaves through hot-water extraction. According to the present invention, the natural antibacterial waterproof composition for soil and wood is applied to the surfaces of the soil wall, soil brick and wood and absorbed therein, thus providing waterproofing performance and protecting the soil wall, soil brick and wood from harmful insects like ants, worms and so on. Further, the composition has excellent waterproofing and insecticidal performance during a long period of time as well as during a short period of time, thus desirably decreasing the maintenance cost.

5 Claims, 5 Drawing Sheets

NATURAL ANTIBACTERIAL WATERPROOF COMPOSITION FOR SOIL AND WOOD AND METHOD FOR MANUFACTURING THE SAME

CROSS REFERENCE

This application claims foreign priority under Paris Convention to Korean Patent Application No. 10-2014-0016560, filed 13 Feb. 2014, with the Korean Intellectual Property Office.

BACKGROUND

The present invention relates to a natural antibacterial waterproof composition for soil and wood and a method for manufacturing the same, and more particularly, to a natural antibacterial waterproof composition for soil and wood and a method for manufacturing the same wherein the composition comprises only natural materials in such a manner as to be applied to soil walls, soil bricks, wood and the like.

As buildings in recent residential environments have been highly developed, cement, concrete, steel frames, and cement adhesives are used rampantly, and in case of closed type buildings for increasing heating efficiencies, a quality of indoor air becomes bad to cause strong alkaline virulence factors of cement and gas and dust harmful to human bodies. Due to harmful gas emitted from the wallpaper bonded by adhesives, further, dwellers have suffered from environmental diseases like atopy, sick building syndrome and so on.

Accordingly, there is a growing interest in eco-friendly construction materials, and especially, an interest in ocher, soil walls and soil bricks used for building traditional houses in a domestic housing culture grows more and more.

Soil is easily obtained around and also one of construction materials leading traditional housing culture. A soil house does not cause any specific pollution during the construction process and is recycled to nature when thrown away. Accordingly, soil is one of excellent eco-friendly construction materials.

However, the construction material made of soil is weak for heavy rain, heavy snow, and torrential rains. Further, the soil is weak for solidity to often cause separation, and dust is easily generated from the soil. As a result, it is hard to make the soil brick or wall only with pure soil.

So as to remove the disadvantages of the soil, accordingly, a soil wall or brick is made by using cement, plaster and inorganic adhesives as a binder, but if the binder is used, advantageous functions of soil such as ventilation, humidity control, antibacterial force and deodorizing become disappear.

Alternatively, a waterproof agent is applied to the soil brick or wall, and the waterproof agent is made of a synthetic rubber resin, thus undesirably losing ventilating capability and humidity control force of soil. Further, the adhesion becomes drastically weak as time is passed, and the soil is easily separated from the soil brick or wall, thus making the waterproofing performance suddenly deteriorated.

So as to over the above-mentioned problems, accordingly, there has been proposed Korean Patent Gazette No. 2003-77473 entitled 'multi-purposed and multi-functional coating composition', wherein the coating composition includes oil and fat components such as perilla oil, tung oil, pine oil and the like, rosin, and turpentine, thus providing excellent waterproofing, water repellency, anti-coloring, mildew resistance, anti-corrosion, and insect repellency. However, if the coating composition is applied to a soil brick or wall, waterproofing performance is a little exerted, but sufficient antibacterial and insecticidal effects are not provided. Further, the waterproofing performance is exhibited during a short period of time, and if the composition is applied to an outdoor wall, the surface of the outdoor wall may be collapsed due to rainwater after a given period of time is passed.

On the other hand, there has been proposed Korean Patent Application Laid-Open No. 2011-0117309 entitled 'natural waterproof composition for soil wall or wood', wherein the composition comprises vegetable oil, rosin, and turpentine, thus improving waterproofing performance, but it does not have any insecticidal effects.

SUMMARY OF THE INVENTION

Accordingly, the present invention has been made in view of the above-mentioned problems occurring in the prior art, and it is an object of the present invention to provide a natural antibacterial waterproof composition for soil and wood and a method for manufacturing the same wherein the composition includes only natural materials, thus improving waterproofing performance, without having any loss in the ventilation, humidity control, and deodorizing function of soil, and further, the composition includes a natural antibacterial insecticide, thus protecting the soil brick or wall from harmful insects.

It is another object of the present invention to provide a natural antibacterial waterproof composition for soil and wood and a method for manufacturing the same wherein the composition is applied to wood used widely as one of construction materials, thus improving antibacterial, insecticidal, and waterproofing performance, To accomplish the above-mentioned objects, according to a first aspect of the present invention, there is provided a natural antibacterial waterproof composition for soil and wood, the composition including: 100 parts by weight of beef tallow; 50 to 150 parts by weight of soybean oil; 20 to 50 parts by weight of turpentine; 100 to 200 parts by weight of pine resin; 20 to 50 parts by weight of paraffin; and 10 to 100 parts by weight of a natural antibacterial insecticide, wherein the natural antibacterial insecticide is made by heating powder of ginkgo leaves and Rhus verniciflura leaves with water, extracting effective components from the powder of ginkgo leaves and Rhus verniciflura leaves through hot-water extraction, and maturing the heated material in the state where the powder of the ginkgo leaves and Rhus verniciflura leaves is contained therein.

To accomplish the above-mentioned objects, according to a second aspect of the present invention, there is provided a natural antibacterial waterproof composition for soil and wood, the composition including: 100 parts by weight of beef tallow; 50 to 150 parts by weight of soybean oil; 20 to 50 parts by weight of turpentine; 100 to 200 parts by weight of pine resin; 20 to 50 parts by weight of paraffin; and 10 to 100 parts by weight of a natural antibacterial insecticide, wherein the natural antibacterial insecticide is made by heating ginkgo leaves and cinnamon with water, extracting effective components from the ginkgo leaves and the cinnamon through hot-water extraction, and mixing pyroligneous liquid to the extracted liquid from which the ginkgo leaves and the cinnamon are removed.

To accomplish the above-mentioned objects, according to a third aspect of the present invention, there is provided a method for manufacturing a natural antibacterial waterproof composition for soil and wood, the method including the steps of: (a) manufacturing a natural antibacterial insecticide with effective components from ginkgo leaves through hot-water extraction; (b) melting 100 to 200 parts by weight of pine resin and 20 to 50 parts by weight of paraffin into 100 parts by weight of beef tallow, dividedly injecting the natural antibacterial insecticide into the melted material over two to ten times, and agitating the melted material in such a manner as to be naturally circulated and melted; (c) maturing the melted material; and (d) heating the matured material and injecting and mixing 50 to 150 parts by weight of soybean oil and 20 to 50 parts by weight of turpentine into the matured material heated, while dividedly injecting the natural antibacterial insecticide into the melted material over two to ten times, wherein 10 to 100 parts by weight of the natural antibacterial insecticide is injected both at the steps (b) and (d), while being divided in half at the steps (b) and (d).

According to the present invention, preferably, the step (a) of manufacturing a natural antibacterial insecticide through hot-water extraction of effective components from ginkgo leaves includes the steps of: (a-1) powderizing the ginkgo leaves and the Rhus verniciflura leaves; (a-2) adding water having a weight 10 to 20 times larger than the powderized ginkgo leaves and Rhus verniciflura leaves to the powder of the ginkgo leaves and Rhus verniciflura leaves and heating the mixture for 10 to 12 hours; and (a-3) maturing the heated material at a temperature of 15 to 30° C. for 20 to 30 hours.

According to the present invention, preferably, the step (a) of manufacturing a natural antibacterial insecticide through hot-water extraction of effective components from ginkgo leaves includes the steps of: (a-1') adding water having a weight 10 to 20 times larger than the ginkgo leaves and the cinnamon to the ginkgo leaves and the cinnamon and heating the mixture for 10 to 12 hours; (a-2') removing the ginkgo leaves and the cinnamon from the heated material; and (a-3') mixing a liquid from which the ginkgo leaves and the cinnamon are removed with pyroligneous liquid.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Figure 1:
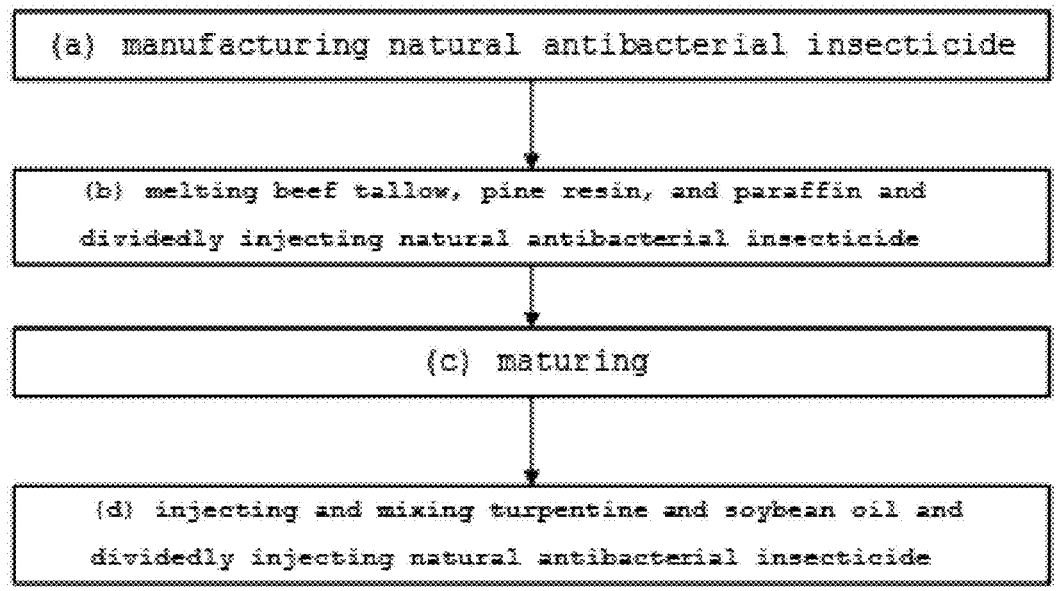
FIG. 1 is a flowchart showing a method for manufacturing a natural antibacterial waterproof composition for soil and wood according to the present invention.

Hereinafter, an explanation on a natural antibacterial waterproof composition for soil and wood and a method for manufacturing the same according to the present invention will be in detail given.

A natural antibacterial waterproof composition for soil and wood according to the present invention is applicable to soil bricks and soil walls made of soil and to wood also used as eco-friendly construction materials.

Since conventional waterproof compositions are made only for the purpose of waterproofing, that is, they are weak for the damages from harmful insects. Further, the conventional waterproof compositions have excellent waterproofing performance during the short period of time, but do not have good waterproofing performance during the long period of time, thus undesirably increasing the maintenance costs.

So as to solve the above-mentioned problems, accordingly, a natural antibacterial waterproof composition for soil and wood according to the present invention includes beef tallow, soybean oil, turpentine, pine resin, paraffin, and a natural antibacterial insecticide, and the natural antibacterial insecticide is made by extracting the effective components from ginkgo leaves through hot-water extraction.

First, the natural antibacterial waterproof composition for soil and wood according to the present invention will be in detail described.

According to the present invention, components having waterproofing performance, such as, beef tallow, soybean oil, turpentine, pine resin, and paraffin, are freely used. If the waterproof composition is made with only one component, the following problem occurs. First, if the waterproof component is not absorbed well into an object to be treated, it is not absorbed easily in the interior of the object, so that a waterproof film or oil film is formed just on the surface of the object. Contrarily, if only the waterproof component having a good absorption rate is used, it is absorbed in the interior of the object, so that the film formed on the surface of the object is not thick to cause the surface of the object to be damaged within a short period of time.

According to the present invention, therefore, the beef tallow, soybean oil, turpentine, pine resin, and paraffin are used with various percentages, thus allowing the waterproofing performance to be exerted over the range from the center of the object to the surface thereof.

At this time, the beef tallow, soybean oil, turpentine, pine resin, and paraffin are not absorbed separately from each other, but they are absorbed in the entire portion of soil or wood through their cooperative action, thus forming the film on the surface of the object. Accordingly, the components show different distribution densities from each other according to their absorption rates.

In this case, the beef tallow as one of the waterproof components contains a lot of unsaturated fatty acids, thus having the highest waterproofing performance in the animal oils and fats. The soybean oil has waterproofing performance and is also acted as a solvent in the composition to decrease the whole viscosity, thus allowing the application and treatment of the composition to be easily conducted. In this case, the soybean oil is added if necessary, and accordingly, it may be not necessarily added.

Further, the pine resin is secreted when a pine tree is damaged. Clear pine resin is transparent liquid, but if time is passed, it becomes milky-white and sticky. In the composition according to the present invention, the pine resin serves to provide waterproofing performance and to assist insecticidal action. Moreover, if the pine resin is applied to the natural antibacterial waterproof composition for soil and wood, a relatively thick and hard film is formed on the soil brick, soil wall, and wood, thus preventing the separation of soil and the generation of dust from the soil, improving the strength of the soil brick and soil wall, and providing harmful insect shielding through the insecticidal effects.

Furthermore, the paraffin as one of the components of the composition according to the present invention has excellent waterproof and water-repellent properties. The paraffin is stably melted with the beef tallow and the soybean oil, thus providing waterproofing performance. Further, the paraffin makes the waterproof layer thick, provides excellent bonding force between the waterproof layer and a base material, and maintains waterproofing performance during a long period of time.

On the other hand, the turpentine used as one of the components of the composition according to the present invention does not serve as any waterproof component, insecticidal component, or antibacterial component, but serves as a solvent, thus ensuring the viscosity of the natural antibacterial waterproof composition for soil and wood. So as to provide high usability, that is, the natural antibacterial waterproof composition for soil and wood according to the present invention should be coated. However, if the viscosity is too high, the usability thereof is lowered, and accordingly, the turpentine is added to lower the viscosity. Furthermore, the coated composition should be rapidly dried, and in this case, since the turpentine is volatile, the drying time is reduced.

According to the present invention, the composition includes 100 parts by weight of beef tallow, 50 to 150 parts by weight of soybean oil, 20 to 50 parts by weight of turpentine, 100 to 200 parts by weight of pine resin, and 20 to 50 parts by weight of paraffin. If the soybean oil has less than 50 parts by weight, the viscosity of the composition is not lowered, but if it exceeds 150 parts by weight, the amount of soybean oil is excessive, thus making the waterproofing performance of the composition deteriorated. If the turpentine has less than 20 parts by weight, the viscosity of the composition is not lowered and the curing thereof is not good, thus making it hard to work. Contrarily, if the turpentine exceeds 50 parts by weight, an amount of solvent is excessive, so that the composition becomes used in large quantities so as to obtain the desired antibacterial and waterproofing performance. Further, if the pine resin has less than 100 parts by weight, it is difficult to prevent the separation of soil and the generation of dust from soil and to maintain the antibacterial and waterproofing performance of the composition during a long period of time. Contrarily, if the pine resin exceeds 200 parts by weight, the amount of pine resin is excessive, which is not economical. If the paraffin has less than 20 parts by weight, it is difficult to maintain the waterproofing performance of the composition during a long period of time, and contrarily, if the paraffin exceeds 50 parts by weight, the amount of paraffin is excessive, which is not economical.

On the other hand, if the composition includes only the above-mentioned waterproofing components, it does not have enough antibacterial and insecticidal effects, thus causing wood to be rotten and making harmful insects stay on soil bricks or walls. Accordingly, the composition of the present invention further includes an antibacterial insecticide.

The antibacterial insecticide used in the composition according to the present invention includes natural components, which is hereinafter referred to as a natural antibacterial insecticide.

According to the present invention, the natural antibacterial insecticide has effective components extracted from ginkgo leaves through hot-water extraction, and so as to enhance antibacterial and insecticidal efficiencies, desirably, different kinds of natural antibacterial insecticides are applied to soil and wood.

First, the natural antibacterial insecticide for soil bricks and walls is extracted from ginkgo leaves and Rhus verniciflura leaves. Water is applied to the ginkgo leaves and Rhus verniciflura leaves pulverized and powderized and then heated, thus extracting effective components from the powder of the ginkgo leaves and Rhus verniciflura leaves through hot-water extrusion, and next, the heated material is matured. At this time, the powder of the ginkgo leaves and Rhus verniciflura leaves is not separated from the extract, thus being penetrated into the pores in the soil bricks or walls. Of course, the antibacterial and insecticidal effects are exerted only with the effective components extracted from the ginkgo leaves and Rhus verniciflura leaves, but if the powder of the ginkgo leaves and Rhus verniciflura leaves is contained therein, the antibacterial and insecticidal effects are more improved. Accordingly, the natural antibacterial insecticide can form a film having excellent weatherproof performance.

To the contrary, wood has smaller pores than the soil bricks or walls, and accordingly, it is hard that the powder of the ginkgo leaves and Rhus verniciflura leaves is penetrated into the pores in the wood. Therefore, water is applied to ginkgo leaves and cinnamon and then heated, thus extracting effective components from the ginkgo leaves and the cinnamon through hot-water extrusion, and next, a liquid from which the ginkgo leaves and the cinnamon are removed is mixed with pyroligneous liquid. In this case, the reason why the Rhus verniciflura leaves are not contained in the composition for the wood is that powder cannot be contained in the composition, and accordingly, the cinnamon and the pyroligneous liquid have more excellent insecticidal effects than the Rhus verniciflura leaves. Of course, the Rhus verniciflura leaves as well as the ginkgo leaves may be all used for the composition for the wood. Also, the cinnamon and the pyroligneous liquid may be used for the composition for the soil bricks or walls. In addition thereto, Phellodendron amurence bark and Rhodohypoxis having antibacterial and insecticidal effects may be additionally added.

An explanation on the method for manufacturing the natural antibacterial insecticide will be in detail given again.

The composition of the present invention includes 10 to 100 parts by weight of natural antibacterial insecticide. If the natural antibacterial insecticide has less than 10 parts by weight, the antibacterial and insecticidal effects are weak, and contrarily, if the natural antibacterial insecticide exceeds 100 parts by weight, the amount of natural antibacterial insecticide is excessive, which is not economical.

As mentioned above, the natural antibacterial waterproof composition for soil and wood according to the present invention is applicable to outdoor soil walls and bricks as well as outdoor and indoor wood. Further, the paraffin and the natural antibacterial insecticide are mixed and melted with the pine resin to make the composition, and accordingly, if the composition is applied to the surface of an object to be treated, it is penetrated into the soil bricks or walls and wood, in a deeper manner than the conventional composition wherein no paraffin and natural antibacterial insecticide are contained, thus forming an oil film on the surface of the object, so that the oil film can be thicker and strong in strength on the surfaces of the soil bricks or walls and wood and the bonding performance of the oil film is improved.

The composition of the present invention is applied to the soil bricks, soil walls, and wood as the construction materials, but it may be of course applied to structures made of soil and wood in various fields.

Now, an explanation on the natural antibacterial waterproof composition for soil and wood and the method for manufacturing the same according to the present invention will be in detail given with reference to the attached drawings. At this time, the mixing ratios of the materials of the composition have been mentioned above, and therefore, an explanation on them will be avoided.

Figure 2:
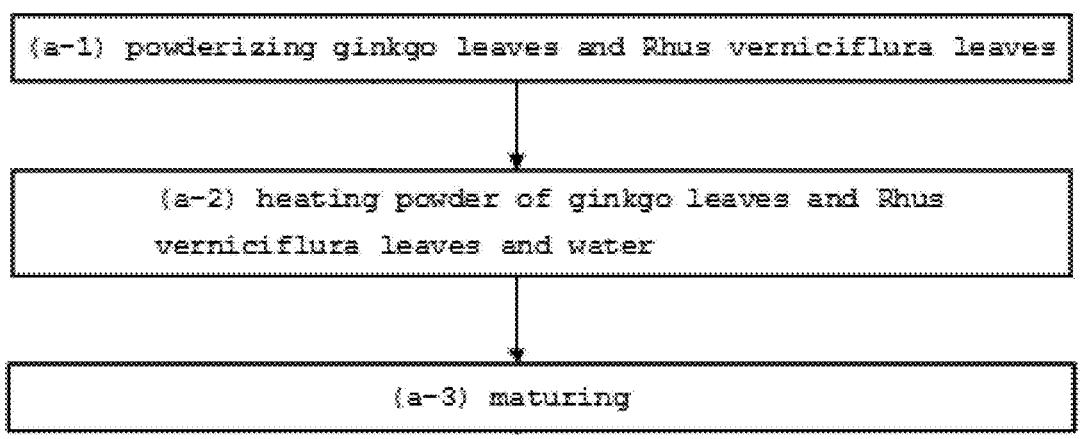
FIG. 2 is a flowchart showing a method for manufacturing a natural antibacterial waterproof composition for soil walls or soil bricks according to the present invention.
Figure 3:
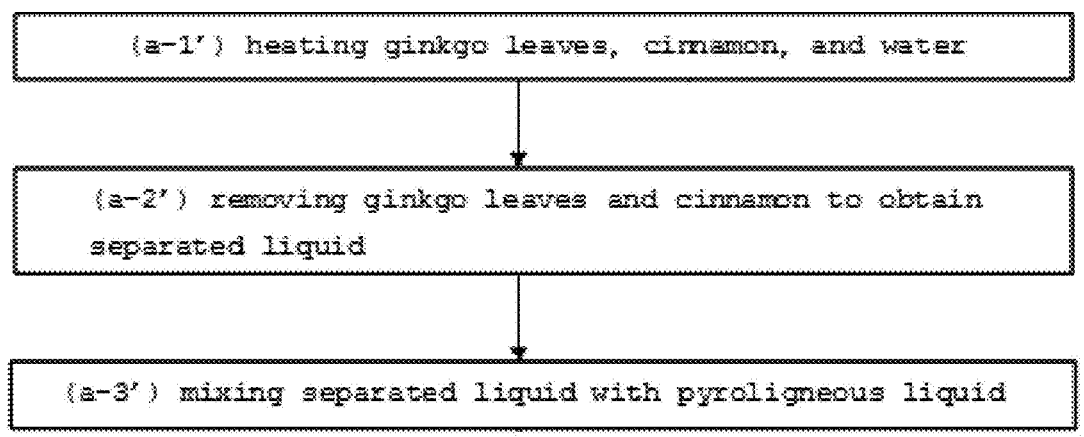
FIG. 3 is a flowchart showing a method for manufacturing a natural antibacterial waterproof composition for wood according to the present invention.

FIG. 1 is a flowchart showing a method for manufacturing a natural antibacterial waterproof composition for soil and wood according to the present invention, FIG. 2 is a flowchart showing a method for manufacturing a natural antibacterial waterproof composition for a soil wall or a soil brick according to the present invention, and FIG. 3 is a flowchart showing a method for manufacturing a natural antibacterial waterproof composition for wood according to the present invention.

Step (a): Manufacturing a Natural Antibacterial Insecticide with Effective Components from Ginkgo Leaves Through Hot-Water Extraction First, a natural antibacterial insecticide is manufactured with effective components extracted from ginkgo leaves through hot-water extraction. The method for manufacturing the natural antibacterial insecticide is divided into the method for wood and the method for soil bricks and walls, which will be in detail described below.

Step (b): Melting Pine Resin and Paraffin into Beef Tallow and Dividedly Injecting the Natural Antibacterial Insecticide into the Melted Material Over Two to Ten Times If the natural antibacterial insecticide is prepared through the step (a), beef tallow is heated, and pine resin and paraffin are injected into the beef tallow and melted therein for 30 to 60 minutes. At this time, the specific gravity of the pine resin and paraffin is smaller than the beef tallow, but since the pine resin and paraffin are injected in the state of being solid, they go down to the bottom of the beef tallow heated. If the beef tallow is continuously heated, the pine resin and paraffin may stick to the bottom surface of a container heated. The sticking is not avoided even by means of artificial agitation. In more detail, the heating temperature of the beef tallow is raised up to 350° C. as a melting point of the beef tallow, but if the pine resin is melted at a high temperature during a long period of time, the pine resin is burnt black from heat even while agitated and stick in the form of ash to the surface of the container.

While the pine resin and the paraffin are being melted in the beef tallow, accordingly, the natural antibacterial insecticide is dividedly injected into the melted material over a plurality of times, that is, two to ten times.

That is, the pine resin and the paraffin are melted in the beef tallow, and if the melting temperature reaches a temperature of 100 to 130° C. at which the pine resin starts to be burnt, a portion of the natural antibacterial insecticide being in a state of a water solution is injected into the melted material. At this time, the natural antibacterial insecticide having higher specific gravity than the beef tallow goes down to the bottom of the container, and since the melting temperature is over the boiling point of water, the water contained in the natural antibacterial insecticide is vaporized and changed to steam. Since the steam is penetrated into the liquid in which the beef tallow, paraffin, and pine resin are melted and evaporated, the beef tallow, paraffin and pine resin in the container are naturally circulated through the process (the evaporation of water), and the melting temperature is momentarily lowered upon the injection of the natural antibacterial insecticide, thus naturally preventing the pine resin from being burnt. Further, even if a small amount of natural antibacterial insecticide is injected, water is vaporized from the bottom surface of the container, and the vaporized steam is penetratedly raised from the melted liquid and collides against the air to allow a portion the vaporized steam to be liquefied. The liquefied water goes down again to the bottom surface of the container by means of the difference of specific gravity, which is repeatedly conducted. Accordingly, the natural circulation of the melted liquid is kept over 10 minutes. Therefore, the temperature upon melting is 350° C. as the melting point of the beef tallow, but the pine resin does not stick to the bottom surface of the container. The melting time is in the range of 30 to 60 minutes.

If the melting is kept in the above-mentioned method, the water contained in the natural antibacterial insecticide is all evaporated, and only the effective components contained therein are melted with the beef tallow, pine resin, and paraffin and become transparent liquid.

Step (c): Maturing the Melted Material

If the melting is finished, the melted material is matured. The maturing is conducted at a temperature of 15 to 30° C. for 48 to 60 hours. The melted material is naturally left, without being separately cooled, and it is slowly reduced in temperature until reaches a maturing temperature. Through the maturing process, the melted material is stabilized and the bonding among the beef tallow, pine resin, paraffin and natural antibacterial insecticide in the melted material is also stabilized.

Step (d): Heating the Matured Material and Injecting and Mixing Soybean Oil and Turpentine into the Matured Material Heated, while Dividedly Injecting the Natural Antibacterial Insecticide into the Melted Material Over Two to Ten Times If the maturing is finished, the matured material is heated again, and soybean oil and turpentine are mixed with the matured material. In the same manner as the above-mentioned step (b), the natural antibacterial insecticide being in the state of the water solution is injected into the mixture over two to ten times, which is conducted for the natural circulation of the mixture. The melting temperature and time at the step (d) are the same as those at the step (b), and if the melting is finished, a clear liquid type composition is obtained.

The composition includes 100 parts by weight of beef tallow, 50 to 150 parts by weight of soybean oil, 20 to 50 parts by weight of turpentine, 100 to 200 parts by weight of pine resin, 20 to 50 parts by weight of paraffin, and 10 to 100 parts by weight of a natural antibacterial insecticide, and since the natural antibacterial insecticide is injected both at the steps (b) and (d), the injected amount thereof is divided in half, so that one portion of the natural antibacterial insecticide is injected by small quantities at the step (b) and the other portion thereof by small quantities at the step (d).

The composition made through the steps (a) to (d) has a type of clear liquid having low viscosity and is applied to soil bricks, soil walls and wood by means of aerosol spraying, thus being easily used and treated.

An amount of the natural antibacterial waterproof composition for soil and wood in use is in the range of 0.5 to 2 $\text{lm}^2$, and after the composition is applied to the soil or wood, it is dried in a shady place.

According to the present invention, the composition can still maintain the advantages of soil and wood as natural construction materials, provide excellent waterproofing and antibacterial effects, and increase the amount of the soil walls, soil bricks or wood construction materials to ensure the structural stability. Further, the composition according to the present invention can prevent the surface of the soil wall or soil brick from being stained with soil and improve the strength of the surface.

Hereinafter, the step (a) for manufacturing the natural antibacterial insecticide through hot-water extraction of the effective components from ginkgo leaves will be in detail explained, while being divided for soil bricks and walls and for wood.

First, as shown in FIG. 2, a method for manufacturing the natural antibacterial insecticide for soil bricks and walls includes the steps of (a-1) powderizing the ginkgo leaves and the Rhus verniciflura leaves, (a-2) adding water having a weight 10 to 20 times larger than the powderized ginkgo leaves and Rhus verniciflura leaves to the powder of ginkgo leaves and Rhus verniciflura leaves and heating the mixture for 10 to 12 hours, and (a-3) maturing the heated material at a temperature of 15 to 30° C. for 20 to 30 hours.

At the step (a-1), the ginkgo leaves and Rhus verniciflura leaves are pulverized and powderized, and so as to conduct easy pulverization, dried ginkgo leaves and Rhus verniciflura leaves are used. At this time, ginkgo leaves and Rhus verniciflura leaves are mixed in a weight ratio of 1:1, and their pulverized particle sizes are not limited specially. Since the pulverized powder should be penetrated into the pores of the soil walls or soil bricks, however, their pulverized particle sizes are desirably in the range of 1 to 100 um.

At the step (a-2), water is applied to the powderized ginkgo leaves and Rhus verniciflura leaves, and the mixture is heated, thus extracting the effective antibacterial and insecticidal components contained in the ginkgo leaves and the Rhus verniciflura leaves. At this time, the heating temperature is desirably in the range of 50 to 100° C. For an initial one hour, the mixture is heated at a high temperature of 80 to 100° C., and after one hour, the mixture is heated at a low temperature of 50 to 80° C., thus preventing the water from being all vaporized. In this case, the reason why the heating time is in the range of 10 to 12 hours is that if the heating time is too short, the time for extracting the effective components is not enough, but if longer than 12 hours, the extraction efficiency is not good. Through this step, further, the powderized ginkgo leaves and Rhus verniciflura leaves can be uniformly distributed in the water solution.

At the step (a-3), next, the heated material is matured at a temperature of 15 to 30° C. for 20 to 30 hours, thus stabilizing the extract, and the extract can be used as a natural antibacterial insecticide. At this time, the powder of ginkgo leaves and Rhus verniciflura leaves is used, without being removed.

The natural antibacterial insecticide has the antibacterial and insecticidal functions with the effective components contained in the ginkgo leaves and the Rhus verniciflura leaves, and the ginkgo leaves have the effective components having antibacterial and insecticidal functions like ginkgo flavone glycosides, and ginkgolides and bilogalides, thus providing excellent antibacterial and insecticidal functions through the composite action of the effective components thereof. Further, the Rhus verniciflura leaves have the effective components like flavonoid, polyphenol and so on, thus providing excellent antibacterial and insecticidal functions through the composite action of the effective components thereof.

Next, as shown in FIG. 3, a method for manufacturing the natural antibacterial insecticide for wood includes the steps of (a-1') adding water having a weight 10 to 20 times larger than the ginkgo leaves and the cinnamon to the ginkgo leaves and the cinnamon and heating the mixture for 10 to 12 hours, (a-2') removing the ginkgo leaves and the cinnamon from the heated material, and (a-3') mixing a liquid from which the ginkgo leaves and the cinnamon are removed with pyroligneous liquid.

At the step (a-1'), first, water having the weight 10 to 20 weight times larger than ginkgo leaves and cinnamon is added to the ginkgo leaves and the cinnamon, and the mixture is heated for 10 to 12 hours. At this time, since the ginkgo leaves and the cinnamon are removed after the extraction of the effective components thereof, there is no separate pulverization process. The heating conditions are the same as those in the step (a-2). The mixture ratio of the ginkgo leaves and the cinnamon is 1:0.5 to 1.

Next, at the step (a-2'), the ginkgo leaves and the cinnamon are separated and removed from the heated material, and at the step (a-3'), the pyroligneous liquid is mixed in the heated material. When considering the effect of the manufacturing cost, it is desirable that 1 to 10 parts by weight of pyroligneous liquid is mixed with respect to 100 parts by weight of the extracted liquid of the ginkgo leaves and cinnamon.

As mentioned above, the ginkgo leaves have the effective components like ginkgo flavone glycosides, and the cinnamon have the effective components like cinnamic aldehyde and salicylaldehyde, thus having insecticidal effects. Further, the pyroligneous liquid is formed by collecting the drops liquefied through the contact between the smoke generated when wood is heated for charcoal production and outside air, thus having excellent deodorizing, antibacterial and insecticidal effects.

Hereinafter, the effects of the composition according to the present invention will be described through examples.

Manufacturing Ocher Brick

Ocher produced from Ilwon, Kimcheon city in Korea was prepared, and impurities were removed from the ocher by means of a filtering screen. Next, the ocher was pressurized by means of a compressor of 70 ton/m$^2$ and molded to a brick, while maintaining an appropriate amount of water therein at a temperature of 25° C., and then, the brick was cured naturally in a shady place for 30 days.

Example 200 g of dried ginkgo leaves and 200 g of Rhus verniciflura leaves were prepared, and they were pulverized to the particle size of 100 um. Next, the pulverized powder was injected into 6000 g of water and heated at a temperature of 80 to 100° C. for one hour, and then, in the state where the heating temperature was reduced to 50 to 80° C., the heating material was heated for 10 hours, while being kept at the heating temperature. After that, the heated liquid was left naturally at a temperature of 20° C. for 20 hours and matured, thus making a natural antibacterial insecticide.

Next, 100 g of beef tallow was heated, and 100 g of pine resin and 40 g of paraffin were injected into the beef tallow. When the heating temperature reached 100° C., 5 g of the prepared natural antibacterial insecticide was injected into the heated material. After that, the above processes were repeatedly conducted ten times for 30 minutes, while the heating temperature was being raised up to 350° C.

Figure 4:
FIG. 4 is a photograph showing the composition according to an Example of the present invention.

Next, the melted material was left and matured at a temperature of 25° C. for 50 hours, and 100 g of soybean oil and 40 g of turpentine were injected into the melted material, while heating the melted material again. When the heating temperature reached 100° C., 5 g of the prepared natural antibacterial insecticide was injected into the heated material. After that, the above processes were repeatedly conducted ten times for 30 minutes, while the heating temperature was being raised up to 350° C. As shown in FIG. 4, as a result, a clear liquid type composition was obtained.

Figure 6:
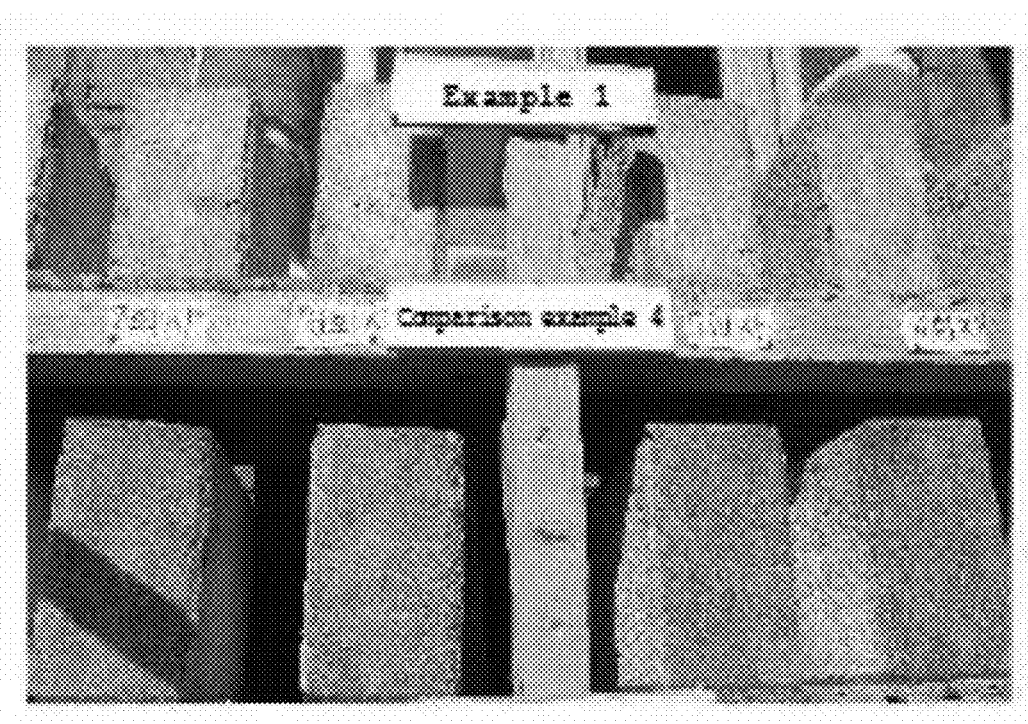
FIG. 6 is a photograph showing the drying processes of the Example of the present invention and the Comparison example 4.

Next, the composition obtained through the Example of the present invention was applied two times to the ocher brick previously made. The total amount of composition applied was 1 l/m$^2$. The ocher brick to which the composition was applied was dried naturally in a shady place for one week. Further, the composition obtained through the Example of the present invention was applied one to ten times to the ocher brick previously made, and next, the ocher brick to which the composition was applied was dried naturally in a shady place for one week. FIG. 6 is a photograph showing the ocher brick naturally dried through the Example of the present invention.

Comparison Example 1

A waterproof agent G made and sold by a company G was applied two times to the ocher brick previously made in the same manner as the Example of the present invention. The total amount of composition applied was 1 l/m². The ocher brick to which the composition was applied was dried naturally in a shady place for one week.

Comparison Example 2

Beef tallow as one of animal oils and fats was prepared, and the beef tallow being in a liquid state was applied two times to the ocher brick previously made in the same manner as the Example of the present invention. The total amount of the beef tallow applied was 1 l/m². The ocher brick to which the beef tallow was applied was dried naturally in a shady place for one week.

Comparison Example 3

Soybean oil as one of vegetable oil was prepared, and the soybean oil was applied two times to the ocher brick previously made in the same manner as the Example of the present invention. The total amount of the soybean oil applied was 1 l/m². The ocher brick to which the soybean oil was applied was dried naturally in a shady place for one week.

Comparison Example 4

Figure 5:
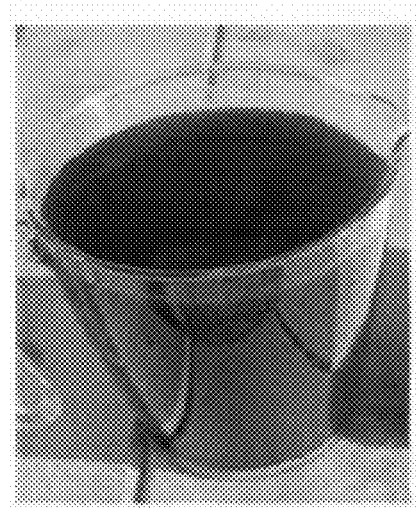
FIG. 5 is a photograph showing the composition according to a Comparison example 4 of the present invention.

First, 100 g of beef tallow was heated, and 100 g of rosin was injected into the beef tallow and melted. The melted material was left and matured at a temperature of 25° C. for 50 hours, and 100 g of soybean oil and 40 g of turpentine were injected into the melted material, while heating the melted material again. The melted material was heated to 350° C., and as a result, a clear liquid type composition was obtained, as shown in FIG. 5.

Next, the composition obtained through the Comparison example 4 was applied two times to the ocher brick previously made. The total amount of composition applied was 1 l/m². The ocher brick to which the composition was applied was dried naturally in a shady place for one week. Further, the composition obtained through the Comparison example 4 was applied one to ten times to the ocher brick previously made, and next, the ocher brick to which the composition was applied was dried naturally in a shady place for one week. FIG. 6 is a photograph showing the ocher brick naturally dried through the Comparison example 4.

Test 1: Test for the Surface and Internal Collapse Due to Dripping Water

So as to check the changes in the surface of a test object due to dripping water, 2 l of water was dripping from 2 m height for 10 minutes. The dripping water for 10 minutes was set to one set, and it was repeatedly conducted until the test object was collapsed. The tests for the Example and the Comparison examples 1 to 4 were conducted over three times.

Figure 7:
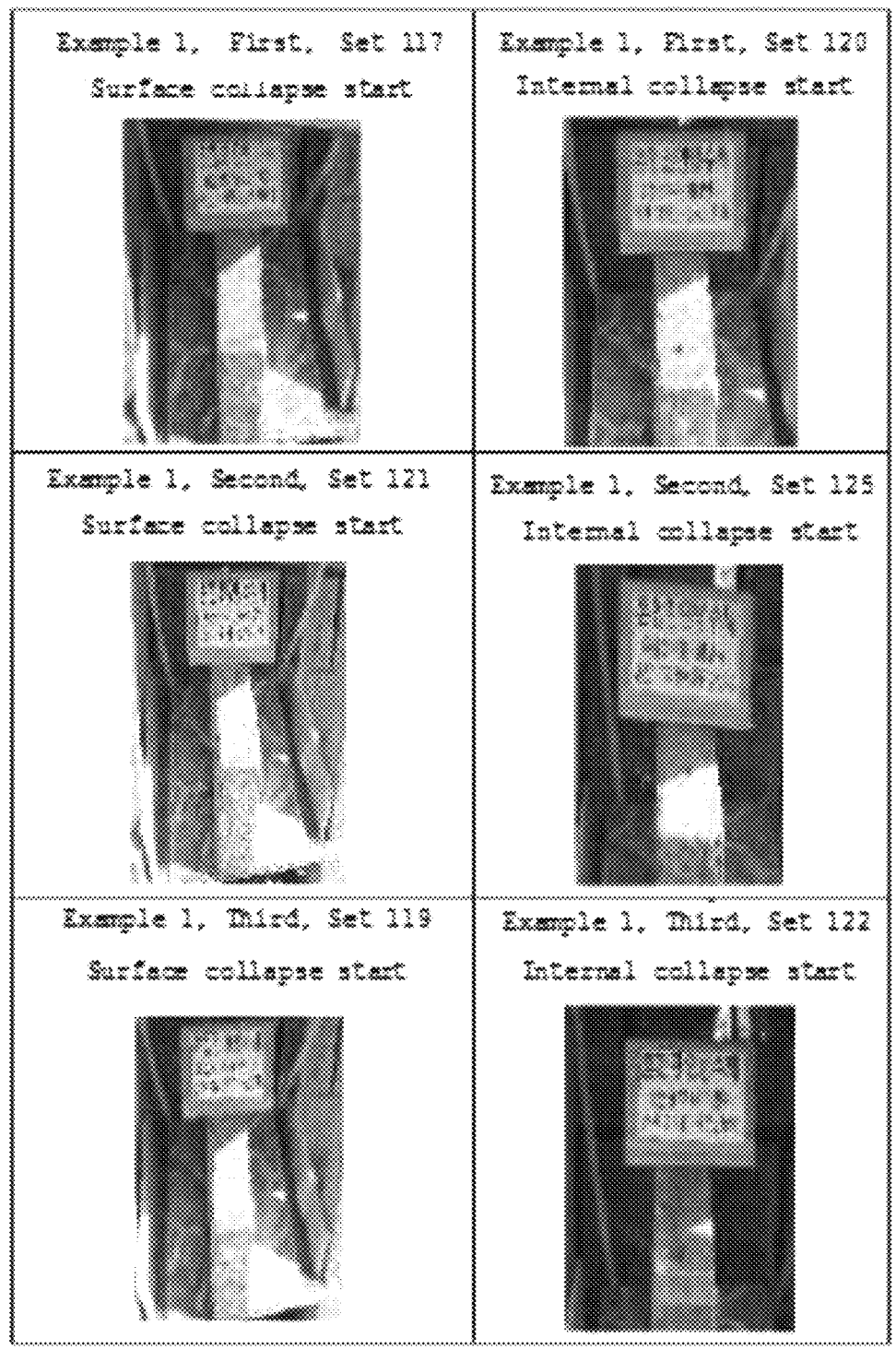
FIG. 7 is a photograph showing dripping water test results of the Example of the present invention.
Figure 8:
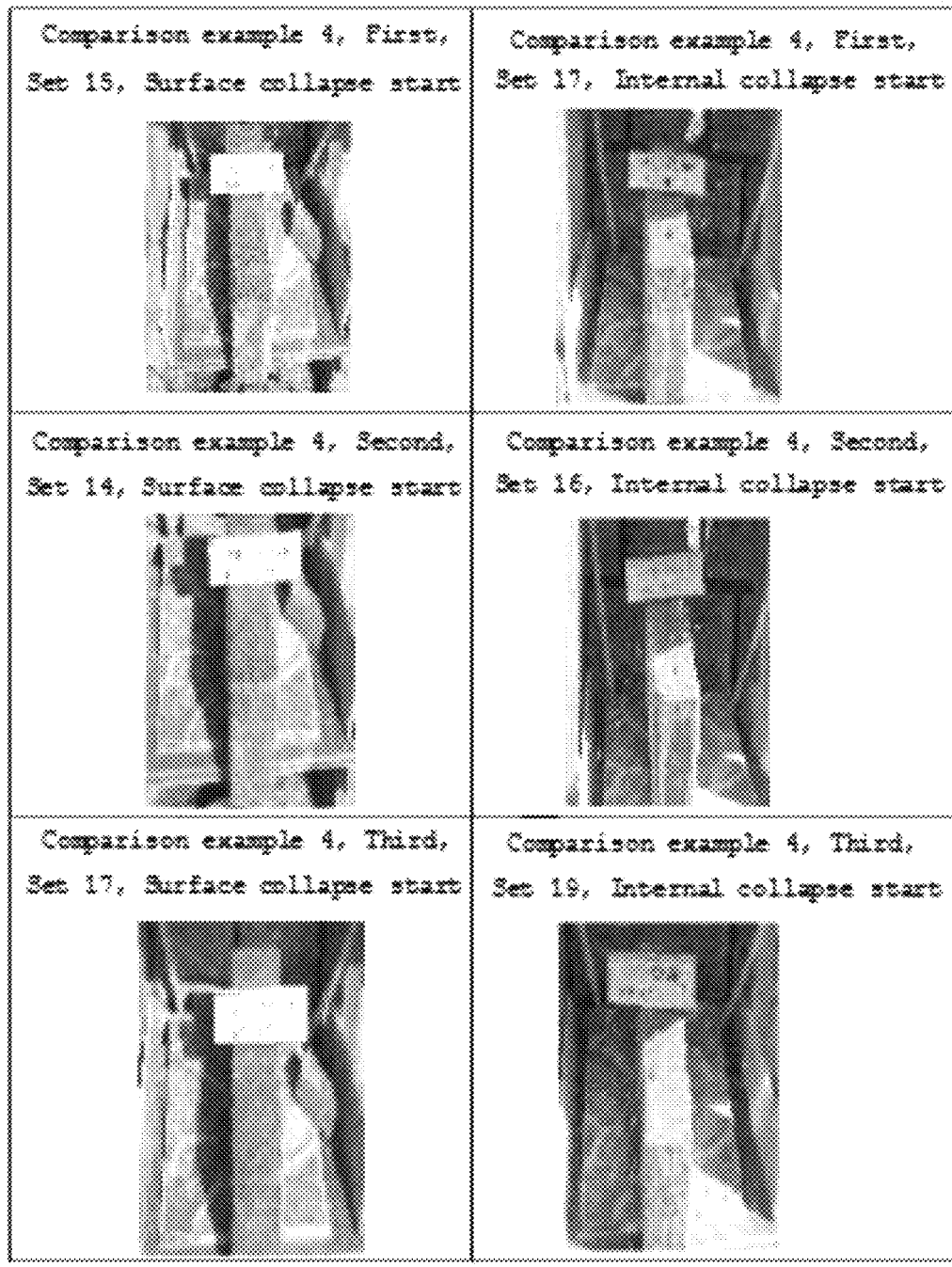
FIG. 8 is a photograph showing dripping water test results of the Comparison examples 1 to 4 of the present invention.

The test results are listed in Tables 1 and 2. FIG. 7 is a photograph showing dripping water test results of the Example of the present invention, and FIG. 8 is a photograph showing dripping water test results of Comparison examples 1 to 4 of the present invention.

TABLE 1

Dripping water test results of Example

| Division | | 1 | 2 | ... | 116 | 117 | 118 | 119 | 120 | 121 | 122 | 123 | 124 | 125 |
|---|---|---|---|---|---|---|---|---|---|---|---|---|---|---|
| Example | 1st | O | O | | O | v | v | v | vX | | | | | |
| | 2nd | O | O | | O | O | O | O | O | v | v | v | v | vX |
| | 3rd | O | O | | O | O | O | v | v | v | vX | | | |

In Table 1, a reference symbol v indicates that surface collapse starts and X indicates that internal collapse starts.

TABLE 2

Dripping water test results of Comparison examples 1 to 4

| Division | | 1 | 2 | ... | 9 | 10 | 11 | 12 | 13 | 14 | 15 | 16 | 17 | 18 | 19 |
|---|---|---|---|---|---|---|---|---|---|---|---|---|---|---|---|
| Comparison Example 1 | 1st | O | vX | | | | | | | | | | | | |
| | 2nd | O | vX | | | | | | | | | | | | |
| | 3rd | O | vX | | | | | | | | | | | | |
| Comparison Example 2 | 1st | O | O | | O | O | v | v | vX | | | | | | |
| | 2nd | O | O | | O | O | O | v | vX | | | | | | |
| | 3rd | O | O | | O | O | O | v | vX | | | | | | |
| Comparison Example 3 | 1st | O | O | | v | v | vX | | | | | | | | |
| | 2nd | O | O | | O | v | vX | | | | | | | | |
| | 3rd | O | O | | O | O | O | v | v | vX | | | | | |
| Comparison Example 4 | 1st | O | O | | O | O | O | O | O | O | v | v | vX | | |
| | 2nd | O | O | | O | O | O | O | O | v | v | vX | | | |
| | 3rd | O | O | | O | O | O | O | O | O | O | O | v | v | vX |

In Table 2, a reference symbol v indicates that surface collapse starts and X indicates that internal collapse starts.

As appreciated from Tables 1 and 2 and FIGS. 7 and 8, the Comparison example 1 shows that the surface and interior of the ocher brick are all collapsed at set 2 over first to third times, the Comparison example 2 shows that the surface and interior of the ocher brick are collapsed at sets 11 to 13, and the Comparison example 3 shows that the surface and interior of the ocher brick are collapsed from set 9 to set 14. On the other hand, the Comparison example 4 having the composition from which paraffin and natural antibacterial insecticide of the Example of the present invention are removed shows that the surface collapse of the ocher brick starts at sets 14, 15 and 17 and the internal collapse of the ocher brick starts at sets 16, 17 and 19. To the contrary, the Example of the present invention shows that no change occurs before set 116. The surface collapse of the ocher brick starts at sets 117, 119 and 121 and the internal collapse of the ocher brick starts at sets 120, 122 and 125. Accordingly, it can be appreciated that the Example of the present invention has more excellent waterproof performance than the Comparison examples 1 to 4.

In case of the Example of the present invention, especially, an oil film is formed to a depth of about 1.2 to 1.5 cm on the surface of the ocher brick, and as the paraffin and natural antibacterial insecticide are mixedly contained in the pine resin, as shown in FIG. 6, the oil film can be remarkably formed thicker than that in the Comparison example 4, so that it can be checked that the oil film is damaged only when 240 l of water is dripping for 1200 minutes through the test results over three times, thus allowing the surface of the ocher brick to be more rigid than those of the conventional waterproof agent and the Comparison examples 1 to 4. That is, it can be appreciated that the surface strength of the ocher brick according to the Example of the present invention is substantially increased.

Test 2: Humidity Control Test

After the ocher brick was coated at a temperature of 13° C. with 500 g of water by means of a spray gun, the time required for natural drying was checked.

As a Comparison example of the Test 2, one piece of marble was coated with 500 g of water by means of a spray gun, and then, the time required for natural drying was checked.

As a result, the ocher brick according to the Example of the present invention emitted water therefrom, and the interior and exterior of the ocher brick were completely dried only within three minutes. However, the marble was completely dried after seven minutes.

Accordingly, it was checked that the composition according to the present invention still maintained the advantages of the ocher brick.

As appreciated from the Tests 1 and 2, it was checked that the composition according to the present invention had excellent waterproof performance and still maintained the inherent advantages of soil.

As described above, the natural antibacterial waterproof composition for soil and wood according to the present invention is applied to the surfaces of the soil wall, soil brick and wood and absorbed therein, thus providing waterproofing performance and protecting the soil wall, soil brick and wood from harmful insects like ants, worms and so on.

Further, the natural antibacterial waterproof composition for soil and wood according to the present invention has excellent waterproofing and insecticidal performance during a long period of time as well as during a short period of time, thus desirably decreasing the maintenance cost.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A natural antibacterial waterproof composition for soil and wood, the composition comprising:
   100 parts by weight of beef tallow;
   50 to 150 parts by weight of soybean oil;
   20 to 50 parts by weight of turpentine;
   100 to 200 parts by weight of pine resin;
   20 to 50 parts by weight of paraffin; and
   10 to 100 parts by weight of a natural antibacterial insecticide,
   wherein the natural antibacterial insecticide is made by heating powder of ginkgo leaves and Rhus verniciflura leaves with water, obtaining extracts from the powder of ginkgo leaves and Rhus verniciflura leaves through hot-water extraction, and maturing the heated material in a state where the powder of the ginkgo leaves and Rhus verniciflura leaves is contained therein.

2. A natural antibacterial waterproof composition for soil and wood, the composition comprising:
   100 parts by weight of beef tallow;
   50 to 150 parts by weight of soybean oil;
   20 to 50 parts by weight of turpentine;
   100 to 200 parts by weight of pine resin;
   20 to 50 parts by weight of paraffin; and
   10 to 100 parts by weight of a natural antibacterial insecticide,
   wherein the natural antibacterial insecticide is made by heating ginkgo leaves and cinnamon with water, obtaining extracts from the ginkgo leaves and the cinnamon through hot-water extraction, and mixing pyroligneous liquid to the extracted liquid from which the ginkgo leaves and the cinnamon are removed.

3. A method for manufacturing a natural antibacterial waterproof composition for soil and wood, the method comprising the steps of:
   (a) manufacturing a natural antibacterial insecticide with extracts from ginkgo leaves through hot-water extraction;
   (b) melting 100 to 200 parts by weight of pine resin and 20 to 50 parts by weight of paraffin into 100 parts by weight of beef tallow, dividedly injecting the natural antibacterial insecticide into the melted material over two to ten times, and agitating the melted material in such a manner as to be naturally circulated and melted;
   (c) maturing the melted material; and
   (d) heating the matured material and injecting and mixing 50 to 150 parts by weight of soybean oil and 20 to 50 parts by weight of turpentine into the matured material heated, while dividedly injecting the natural antibacterial insecticide into the melted material over two to ten times, wherein 10 to 100 parts by weight of the natural antibacterial insecticide is injected both at the steps (b) and (d), while being divided in half at the steps (b) and (d).

4. The method for manufacturing a natural antibacterial waterproof composition for soil and wood according to claim 3, wherein the step (a) of manufacturing a natural antibacterial insecticide through hot-water extraction from ginkgo leaves comprises the steps of:
   (a-1) powderizing the ginkgo leaves and Rhus verniciflura leaves;

(a-2) adding water having a weight 10 to 20 times larger than the powderized ginkgo leaves and Rhus verniciflura leaves to the powder of the ginkgo leaves and Rhus verniciflura leaves and heating the mixture for 10 to 12 hours; and (a-3) maturing the heated material at a temperature of 15 to 30° C. for 20 to 30 hours.

5. The method for manufacturing a natural antibacterial waterproof composition for soil and wood according to claim 3, wherein the step (a) of manufacturing a natural antibacterial insecticide through hot-water extraction from ginkgo leaves comprises the steps of:

(a-1') adding water having a weight 10 to 20 times larger than the ginkgo leaves and cinnamon to the ginkgo leaves and the cinnamon and heating the mixture for 10 to 12 hours;

(a-2') removing the ginkgo leaves and the cinnamon from the heated material; and (a-3') mixing a liquid from which the ginkgo leaves and the cinnamon are removed with pyroligneous liquid.

* * * * *